United States Patent [19]

Kikuchi et al.

[11] Patent Number: 4,690,156

[45] Date of Patent: Sep. 1, 1987

[54] APPLICATOR FOR LOCALIZED HYPERTHERMIA BY ELECTROMAGNETIC WAVES

[75] Inventors: Makoto Kikuchi, 16-9, Inokashira 1-chome, Mitaka-shi, Tokyo; Shinsaku Mori, 31-6, Okusawa 1-chome, Setagaya-ku, Tokyo; Yoshio Nikawa, 26-14, Nerima 2-chome, Nerima-ku, Tokyo; Takashige Terakawa, Tokyo, all of Japan

[73] Assignees: Tokyo Keiki Co., Ltd.; Makoto Kikuchi; Shisaku Mori; Yoshio Nikawa, all of Tokyo, Japan

[21] Appl. No.: 707,445

[22] Filed: Mar. 1, 1985

[30] Foreign Application Priority Data

Mar. 4, 1984 [JP] Japan .................................. 59-40797
Mar. 4, 1984 [JP] Japan .................................. 59-40798
Mar. 4, 1984 [JP] Japan .................................. 59-40799
Apr. 28, 1984 [JP] Japan ................................. 59-86921
Apr. 28, 1984 [JP] Japan ................................. 59-86922

[51] Int. Cl.$^4$ ............................................. A61N 5/00
[52] U.S. Cl. ............................... 128/804; 219/10.55 R
[58] Field of Search ...................... 128/804, 399, 328; 219/10.55 R, 10.55 A, 10.55 F; 343/753, 786; 350/418

[56] References Cited

U.S. PATENT DOCUMENTS

| 3,077,195 | 2/1963 | Folsche | 128/804 |
|---|---|---|---|
| 4,108,147 | 8/1978 | Kantor | 128/804 |
| 4,140,130 | 2/1979 | Storm, III | 128/804 |
| 4,204,549 | 5/1980 | Paglione | 128/804 |
| 4,228,809 | 10/1980 | Paglione | 128/804 |
| 4,282,887 | 8/1981 | Sterzer | 128/804 |
| 4,341,227 | 7/1982 | Turner | 128/804 |
| 4,397,313 | 8/1983 | Vaguine | 128/804 |
| 4,397,314 | 8/1983 | Vaguine | 128/804 |
| 4,403,618 | 9/1983 | Vaguine | 128/804 |
| 4,446,874 | 5/1984 | Vaguine | 128/804 |
| 4,462,412 | 7/1984 | Turner | 128/804 |
| 4,530,358 | 7/1985 | Forssmann et al. | 128/328 |
| 4,586,516 | 5/1986 | Vaguine | 128/804 |
| 4,589,424 | 5/1986 | Vaguine | 128/804 |

FOREIGN PATENT DOCUMENTS

| 0111314 | 6/1984 | European Pat. Off. | |
| 1440333 | 4/1969 | Fed. Rep. of Germany | |
| 2060923 | 7/1971 | Fed. Rep. of Germany | 343/753 |
| 2648908 | 5/1978 | Fed. Rep. of Germany | 128/804 |
| 0028338 | 3/1977 | Japan | 350/418 |

OTHER PUBLICATIONS

"A Microwave System . . . " by Magin, IEEE Transactions Microwave Theory and Technology MTT-27, No. 1, pp. 78–83, Jan. '79.

"Techniques . . . Hyperthermia . . . Carcinoma" by Robinson et al., IEEE Transactions Microwave Theory and Technology, MTT-26, No. 8, pp. 546–549, Aug. '78.

"Hyperthermia in Cancer Therapy" by Storm, C. K. Hall Med. Pub., 1983 "A Localized Current Field . . . " by Astrahan et al., Med. Phys 9(3), May/Jun. 1982, pp. 419–424.

NASA Technical Brief, p. 59, Spring 1980.
The Oct. 1976 issue of Microwaves, article entitled: "Microwaves Score TKO in Fight Against Cancer".

Primary Examiner—Lee S. Cohen
Attorney, Agent, or Firm—Sandler & Greenblum

[57] ABSTRACT

Coolant liquid is caused to flow through a lens section of an applicator to control the heating of the applicator due to a loss in propagation of the electromagnetic waves in the applicator. Furthermore, in this applicator, device for decreasing the internal loss, device for improving a lens effect to efficiently heat a predetermined portion in a living body, and the like are provided, respectively, as necessary.

16 Claims, 45 Drawing Figures (1)    (2)

(1)

(2)

(1)

(2)

(3)

(1)

(2)

(3)

(1)

(2)

APPLICATOR FOR LOCALIZED HYPERTHERMIA BY ELECTROMAGNETIC WAVES

BACKGROUND OF THE INVENTION

1. Field of the Invention

This invention relates to an applicator for a heating treatment, and particularly, to an applicator for a heating treatment, wherein a predetermined portion in a living body is locally heated for treatment by the electromagnetic waves.

2. Description of the Prior Art

In recent years, the heating treatment, which may be referred to as "Hyperthermia", has been highlighted. There have been successive research reports to the effect that, particularly, a malignant tumor is continuously heated at about 43° C. for one or two hours for example, and this treatment is repeated in predetermined cycles, whereby the regenerating function of a cancerous tissue is hampered, so that the most part of the cancerous tissue can be killed (F. K. Storm: Hyperthermia In Cancer Therapy, C. K. Hall Med. Pub. Boston (1983)). The heating treatment of this type is divided into two parts including a generally heating treatment and a localized heat treatment. For the localized heating treatment, wherein only cancerous tissue and therearound are selectively heated, a method of heating by the electromagnetic waves, a method of heating by the electromagnetic induction, a method of heating by the ultrasonic waves, and the like, have been proposed.

On the other hand, the inventors of the present invention have heretofore been proposing the effectiveness, in the case of heating a cancer in the deep portion of the living body, of treatment by electromagnetic waves and have been researching along this line. In this case, for the applicator for delivering the electromagnetic waves into the living body, the inventors have adopted a method of providing therewith an electromagnetic lens necessary to focus the energy of the electromagnetic waves. More specifically, as shown in FIGS. 1 and 2, an applicator 1 includes an electromagnetic wave feed section 2, a case body waveguide section 3 and an electromagnetic lens section 4 provided in an electromagnetic horn. An output stage of this electromagnetic lens section 4 is provided with a solid cooling plate 5 for preventing the surface of the living body from being overheated, and the solid cooling plate 5 may be cooled by cooling water. As shown, in FIG. 2, in the electromagnetic lens section 4, there are provided metal plates 6A, 6A, . . . at regular intervals 'a'. The sides of the metal plates 6A which receive the electromagnetic waves are formed generally concavely as shown in FIG. 3 for converting the spherical electromagnetic waves delivered from the feed section 2 into the planar electromagnetic waves. Further, to focus planar waves formed through the action of the concave portion, in the central portion of the discharging sides of the electromagnetic lens section 4, there are arranged shorter metal plates as shown in FIG. 4, whereby the metal plates are generally concavely arranged and fixed.

On the other hand, the conventional example presents the following disadvantages.

(1) In considering the transmission system for the applicator as a whole, not shown, including electromagnetic wave generating means such as a magnetron or the like, the interior of the applicator would become heated and output from the applicator disadvantageously decreased, if the electromagnetic waves in the applicator are not matched with the generated waves. This occurs because the reflected waves would increase to generate standing waves.

(2) In the waveguide portion of the feed section 2 and the waveguide portion of the electromagnetic section 4, the propagated energy is concentrated at the central portion of the respective waveguides as shown in FIG. 5(1), and the concentrated energy, as it is, is delivered to the electromagnetic lens section 4, so that an original lens effect cannot be satisfactorily displayed in the electromagnetic lens section 4. More specifically, if the electromagnetic waves shown in FIG. 5(1) (now, the electromagnetic waves are assumed to be microwaves of $TE_{10}$ mode), as they are, are delivered into the electromagnetic lens section 4 for example, then the intensities of the excitation in the respective zones partitioned by the intervals 'a' are 0.90, 0.62 and 0.22, respectively, when the field intensities are normalized in the center zone in consideration of dividing the interior of the waveguide 3 into seven parts, whereby a distribution as shown in FIG. 5(2) is obtained. Because of this, the distribution of energy on the side of the inner wall of the waveguide is small, whereby satisfactorily focused electromagnetic waves cannot be formed in the electromagnetic lens section 4, thus presenting a disadvantage such that heating of the deep portion in the living body is hampered.

(3) In the waveguide portion, the inner dimension of the propagated electromagnetic waves in a direction of the magnetic field component must be set within a range between one half wavelength and one wavelength from the relationship of transmitting propagation. In consequence, when consideration is given to the case where the interior of the applicator forms a cavity, i.e. the interior is filled up with a gas such as air for example, one half wavelength substantially equals to 50 cm when a frequency used is 300 $MH_Z$. Because of this, when a rapid treatment is required in particular, the applicator as a whole would need to be large in size, thus presenting the disadvantages that difficulties are encountered in handling the applicator, an appliance for fixing the applicator to the living body would also need to be large and rapid treatment is impracticable.

(4) Bubbles are stagnant in the applicator when it is used for a long period of time, whereby output of the electromagnetic waves from the applicator is disadvantageously decreased with time.

(5) In treating a cancer in the living body, there are many cases where the central portion of the cancer is shifted from a position at which applicator is fixed. In such cases, it takes much labor to detect the central position of the cancer and to fix the applicator onto the living body, thus presenting a disadvantage in that rapid treatment cannot be done.

SUMMARY OF THE INVENTION

An object of the present invention is to provide an applicator for a heating treatment for efficiently irradiating the energy of electromagnetic waves onto a cancerous tissue formed within a living body in particular by use of an electromagnetic lens for a predetermined period of time to thereby conduct localized heating.

Another object of the present invention is to provide an applicator for a heating treatment, wherein coolant liquid is caused to flow from the outside through an electromagnetic lens section provided in a case body of the applicator, the heating of the applicator by internal reflection, and the like, of electromagnetic waves can be controlled and the handling of the applicator is easy.

A further object of the present invention is to provide an applicator for a heating treatment, wherein, to reduce reflection of electromagnetic waves in the case body of the applicator, the methods adopted are such that matching layers are provided in the applicator, the applicator is filled up with a dielectric material or materials low in attenuation of electromagnetic waves, or the like, and the output of the applicator is thereby improved.

A still further object of the present invention is to provide an applicator for a heating treatment for practical use, wherein, to improve the lens effect by use of an electromagnetic lens section, a dielectric plate is provided on the inner wall of a case body of the applicator, distributing plates are provided in the applicator, dielectric plates are provided on opposite surfaces of a plurality of metal plates forming the electromagnetic lens section, and means are provided for extracting bubbles generated in the applicator to the outside of the applicator.

A still more further object of the present invention is to provide an applicator for a heating treatment for practical use, wherein an electromagnetic lens section is detachable from a case body of the applicator so that any one of the electromagnetic lens sections can be selectively used to match the position and shape of an effected part of a living body, or a plurality of metal plates constituting the electromagnetic lens section are made rotatable, respectively.

A yet further object of the present invention is to provide an applicator for a heating treatment arrange such that a cooling mechanism is provided at the opening of a case body of the applicator to control elevation of temperature on the surface of a living body, generated due to an increased output, and a flexible dielectric sheet relatively low in attenuation of the electromagnetic waves is sealingly mounted to the cooling mechanism on the side of the living body or is fastened to a surface being in contact with the living body to improve the adhesion of the cooling mechanism to the surface of the living body.

BRIEF DESCRIPTION OF THE DRAWINGS

FIGS. 1 to 5 are views in explanation of the examples of the prior art, in which, FIG. 1 is a perspective view showing the conditions as used, FIG. 2 is an explanatory view showing the electromagnetic lens section provided in an applicator shown in FIG. 1, FIGS. 3 and 4 are views in explanation of actions of FIG. 2, respectively, and FIGS. 5(1), (2) are explanatory views showing the state of propagation of the electromagnetic waves in the waveguide shown in FIGS. 1 and 2;

DETAILED DESCRIPTION OF THE PREFERRED EMBODIMENT (First Embodiment)

Figure 6:
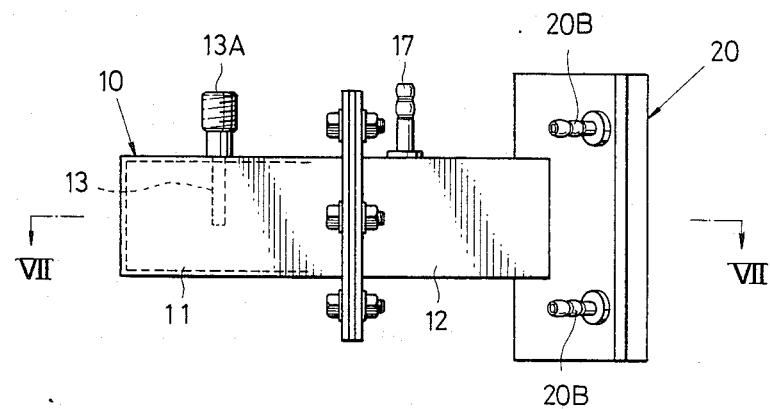
FIG. 6 is a front view showing a first embodiment of the present invention.
Figure 7:
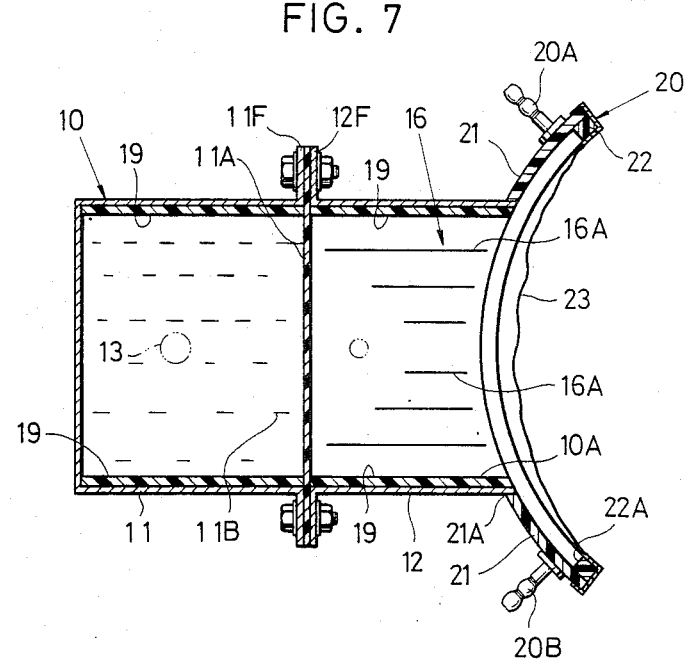
FIG. 7 is a sectional view taken along the VII—VII in FIG. 6.

Description will hereunder be given of the first embodiment of the present invention with reference to FIGS. 6 and 7. Reference is also made to co-pending application Ser. No. 878,328 filed June 25, 1986 entitled APPLICATOR FOR THE USE IN HYPERTHERMIA and assigned to the same assignee as the present application.

Referring to these drawings, designated at 10 is a case body and at 20 is a cooling mechanism. The case body 10 is constituted by a feed section waveguide 11 and a lens section waveguide 12. In the feed section waveguide 11 there are provided an exciting antenna 13 and a coaxial connector 13A. Because of this, electromagnetic waves delivered through the coaxial connector 13A are efficiently introduced into the case body 10. The feed section waveguide 11 is filled up with machine oil 11B which is a dielectric material low in attenuation of the electromagnetic waves, in this embodiment. Denoted at 11A is a dielectric plate for sealing the machine oil in. This dielectric plate 11A is formed of a material being relatively low in attenuation of the electromagnetic waves.

On the other hand, the lens section waveguide 12 is open at opposite end portions thereof to the right and left in the drawing, provided therein with an electromagnetic lens section 16, and equipped at the center of the exterior thereof with flowin-flowout portion 17 for cooling water, as shown. In the electromagnetic lens section 16 metal plates 16A, 16A, ... are used which are different in length from one another. The metal plates 16A, 16A, ... are disposed equidistantly from one another in such a manner that the shorter metal plates 16A are arranged in the central portion of the electromagnetic lens section 16 and the longer metal plates 16A are disposed close to the sides of opposing inner walls as shown in FIG. 7. Because of this, the electromagnetic waves delivered to the electromagnetic lens section 16 are gradually divided from the metal plates 16A on the sides of the inner walls to the whole area, so that an electromagnetic lens section 16 which is high in matching effect can be obtained.

Figure 8:
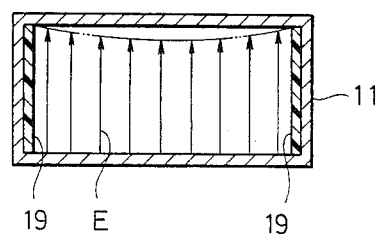
FIGS. 8(1), (2) are explanatory views showing the uniformalizing of the field intensities through the action of the dielectric plate provided on the inner wall of the case body, respectively.
Figure 8:
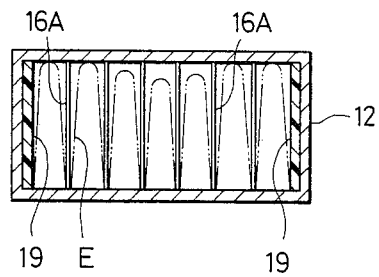

A dielectric plate 19 relatively high in dielectric constant and low in attenuation is provided on the inner wall of the case body 10 in parallel to the direction (the direction parallel to the antenna 13) of the electric field of the electromagnetic waves. As shown in FIG. 8, the disadvantage of the prior art that the energy of the electromagnetic waves is concentrated only at the center (Refer to FIG. 5) can be improved to a considerable extent.

The cooling mechanism 20 includes an abutment support plate 21 formed of a dielectric plate and curved along the living body (refer to A in FIG. 1), an abutting plate 22 solidly secured to the outer surface of the abutment support plate 21, and a flexible film member 23 sealedly mounted to the outer surface of the abutting plate 22. A square through-hole 21A abutting an irradiation opening 10A of the case body 10 is formed in the central portion of the abutment support plate 21, and a square cutaway hole 22A larger than this through-hole 21A is formed in the abutting plate 22 as shown in FIG. 7, so that coolant liquid can very naturally flow between the interiors of the case body 10 and the cooling mechanism 20. When the abutment support plate 21 is formed to suit the surface of the living body, the flexible film member is removed and the coolant liquid may be directly applied to the surface of the living body.

Water (relative dielectric constant $\epsilon\gamma=80.36$, provided that at 20° C. and measured wavelength $\infty$) is used as the coolant liquid in the cooling mechanism 20 in this embodiment. A plurality of coolant flowin-flowout portions 20A and 20B are arranged in symmetry on the peripheral end portion of the cooling mechanism 20, so that the flowing direction of the coolant liquid can be suitably selected. Designated at 11F and 12F are detachable flange portions.

In the first embodiment with the above-described arrangement, because a construction is provided which has satisfactory impedance matching, in which reflection is low from the exciting antenna 13 to the outer end of the electromagnetic lens section 16, the present invention is advantageous in that the electromagnetic waves delivered from the means for generating the electromagnetic waves, such as a magnetron or the like, are efficiently focused and irradiated to the outside. Particularly, the electromagnetic feed section waveguide 11 is filled up with the machine oil, so that the size of the electromagnetic feed section waveguide 11 can be made to be $1\sqrt{\epsilon\gamma}$, i.e., about ⅔ (provided that the relative dielectric constant of machine oil $\epsilon\gamma\approx 2.2$). As a consequence, the first embodiment is generally made compact in size and formed into a split type, whereby the embodiment is advantageous in that the electromagnetic lens sections having cooling mechanisms of various types are prepared in advance, so that the electromagnetic lens section most suitable for a treated portion of a living body can be selectively used.

(Second Embodiment)

Figure 9:
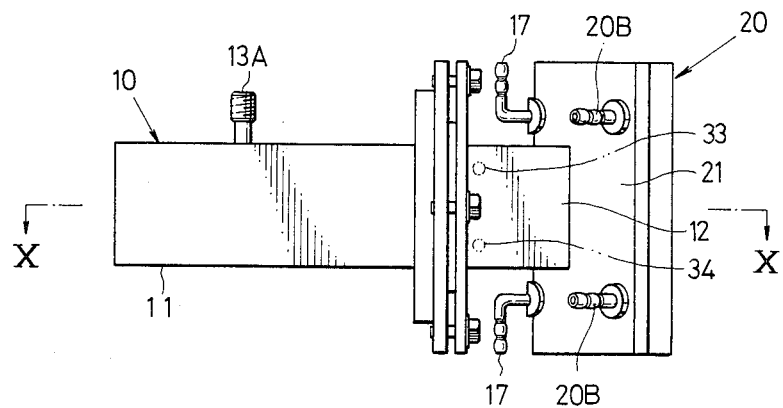
FIG. 9 is a front view showing a second embodiment of the present invention.
Figure 10:
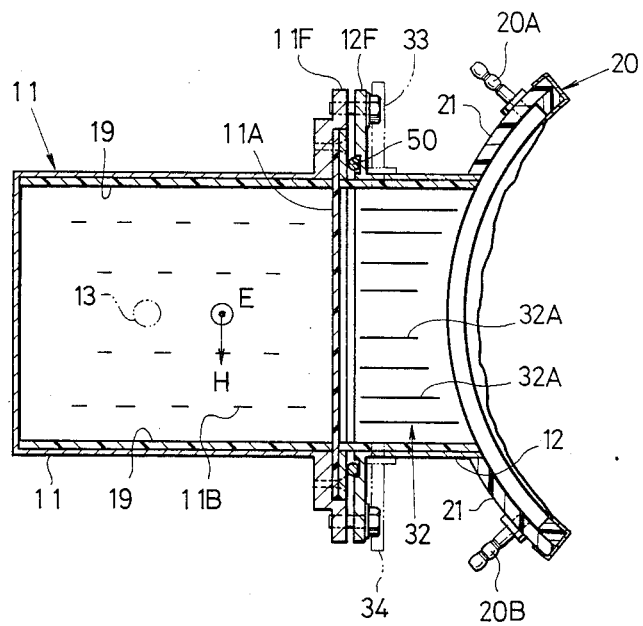
FIG. 10 is a sectional view taken along the line X—X in FIG. 9.

Description will hereunder be given of the second embodiment of the present invention with reference to FIGS. 9 and 10.

As shown in FIG. 9, the coolant flowin-flowout portions 17 are provided at the upper and lower end portions of the central portion in the rear surface of the abutment support plate 21, and an electromagnetic wave transmission path of the electromagnetic lens section 32 is shortened so as to lower the attenuation of the electromagnetic waves.

More particularly, in the electromagnetic lens section 32, a plurality of metal plates 32A, 32A, ... are equidistantly arranged, and the metal plates 32A disposed at the outer side portions are longer than those disposed at the inner portion. Denoted at 33 and 34 are deaerating means. These deaerating means 33 and 34 are adapted to allow the coolant liquid in the interior to flow out therethrough constantly in small quantities, whereby internal bubbles are released to the outside. Designated at 50 is a seal member. In the second embodiment, the respects other than the above are identical with those in the first embodiment.

The second embodiment is advantageous in that, in addition to obtaining the functional effects identical with the first embodiment, the electromagnetic lens section 32 can be provided along the curved surface of the abutment support plate 21 of the cooling mechanism 20, so that, generally, the total length of the case body 10 can be shortened and the portion of the feed section waveguide 11 can be lengthened, thereby enabling to lower the attenuation of the electromagnetic waves.

(Third Embodiment)

Figure 11:
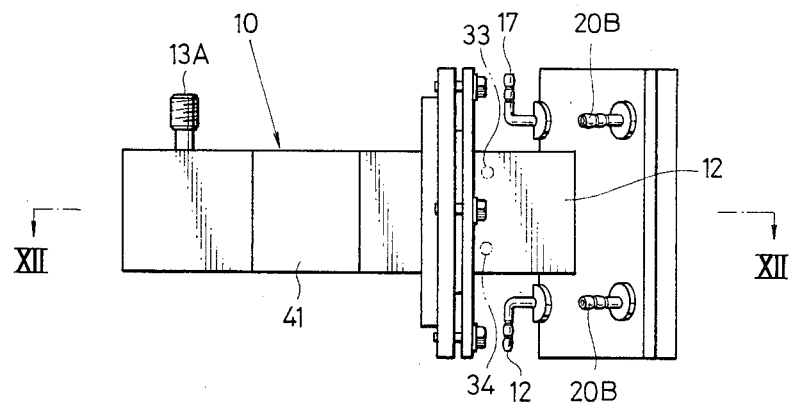
FIG. 11 is a front view showing a third embodiment of the present invention.
Figure 12:
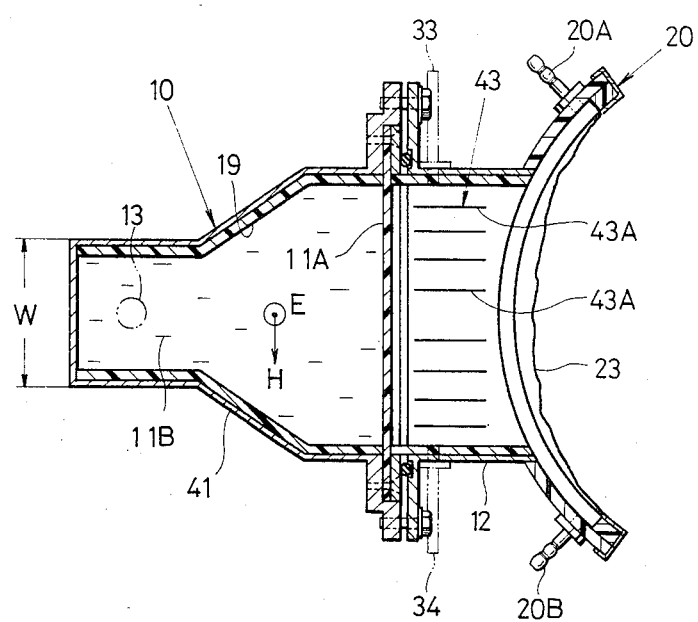
FIG. 12 is a sectional view taken along the line XII—XII in FIG. 11.

Description will hereunder be given of the third embodiment of the present invention with reference to FIGS. 11 and 12. This embodiment is to be used in the case where the electromagnetic waves have relatively high frequencies, are used wherein a width W of the portion of the feed section waveguide 41 is smaller one compared with the preceding embodiments and the electromagnetic lens section 43 is more compact in size. In this case, metal pieces 43A, 43A, ... identical having the same dimensions as one another are used in the electromagnetic lens section 43 and the intervals therebetween are narrower from the inner sides toward the outer sides. In the third embodiment, the respects other than the above are identical with those in the second embodiment.

The third embodiment is advantageous in that, in addition to obtaining the functional effects identical with the second embodiment, generally, the third embodiment can be compact in size and light in weight in association with the electromagnetic waves high in frequency, whereby the handling becomes easy, so that the treatment can be facilitated.

In the first to third emboidments, there is shown examples of the cases in which the machine oil 11B is used as the dielectric material to fill up the electromagnetic wave feed section waveguide 11 or 41. However, the present invention need not necessarily be limited to this, and a solid or semi-solid dielectric material low in attenuation may be used.

Additionally, in the first to third embodiments, there is shown examples of an applicator for use in a treatment of heating a cancer effected part in a living body in particular. However, the cooling mechanism 20, the dielectric plate 19 and the electromagnetic lens section 16 may be removed when a cancer is located on the surface of the living body or an internal portion in the living body is slowly heated for treatment, since there is no necessity for focusing the electromagnetic waves. This arrangment is advantageous in that the applicator may be made compact in size and the handling thereof is easy.

(Fourth Embodiment)

Figure 13:
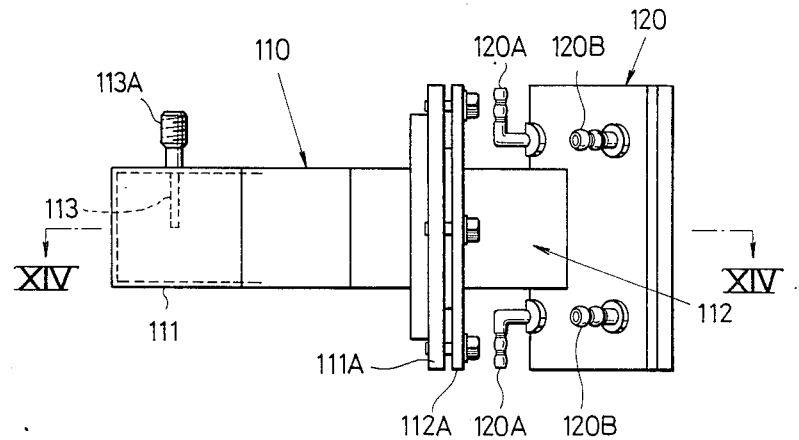
FIG. 13 is a front view showing a fourth embodiment of the present invention.
Figure 14:
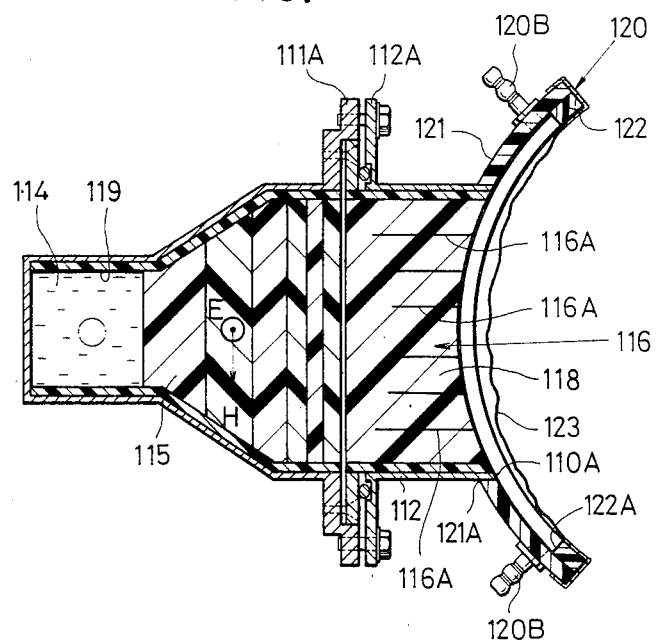
FIG. 14 is a sectional view taken along the XIV—XIV in FIG. 13.

Description will hereunder be given of the fourth embodiment of the present invention with reference to FIGS. 13 and 14.

Referring to these drawings, designated at 110 is a case body and at 120 is a cooling mechanism. The case body 110 is constituted by a feed section waveguide 111 and a lens section waveguide 112. The feed section waveguide 111 is provided with an exciting antenna 113 and a coaxial connector 113A. The exciting antenna 113 is filled up therearoound with a dielectric material 114 low in attenuation, such as oil. In the feed section waveguide 111, from this dielectric material 114 to the lens section waveguide 112, stratified matching layers 115 are provided consisting of a plurality of dielectric plates, so that the electromagnetic waves can be efficiently delivered to the side of the lens section waveguide 112. Furthermore, in the matching layers 115, materials having predetermined dielectric constants different from one another are selectively used so that the dielectric constant becomes gradually larger from the exciting antenna 113 toward the lens section waveguide 112.

The lens section waveguide 112 is filled up over the entire area thereof with a solid or semi-solid dielectric material 118 having a dielectric constant approximate to that of a living body which is low in attenuation of the electromagnetic waves, so that the portion of the lens section waveguide 112 can be made compact in size and matched with the living body. In this lens section waveguide 112, an electromagnetic lens section 116 is provided consisting of a plurality of metal plates 116A, 116A, . . . for focusing the energy of electromagnetic waves on an object in the living body. The metal plates 116A, 116A, . . . are different in length from one another in such a manner that the shorter metal plates 116A are arranged in the central portion and the longer metal plates 116A are arranged on the sides of the inner walls. The metal plates 116A are disposed equidistantly from one another. As the result, the electromagnetic waves delivered to the electromagnetic lens section 116 are gradually divided from the metal plates 116A on the sides of the inner walls to a whole area, so that the electromagnetic lens section 116 which is relatively high in matching effect can be obtained.

Furthermore, a dielectric plate 119 which is relatively high in dielectric constant and low in attenuation is provided on the inner wall of the case body 110 in a direction parallel to the direction E of the electric field of the electromagnetic waves. With this arrangement, the situation where the energy of the electromagnetic waves is concentrated only at the center can be avoided.

Further, the cooling mechanism 120 includes an abutment support plate 121 formed of a dielectric plate and curved along the living body (refer to A in FIG. 1), an abutting plate 122 solidly secured to the other surface of the abutment support plate 121, and a flexible film member 123 sealedly mounted to the outer surface of the abutting plate 122. A square through-hole 121A abutting an irradiation opening 110A of the case body 110 is formed in the central portion of the abutment support plate 121, and a square cutaway hole 122A larger than this through-hole 121A is formed in the abutting plate 122 as shown in FIG. 14 so that coolant liquid can very naturally flow between the interiors of the case body 110 and the cooling mechanism 120.

Water (relative dielectric constant $\epsilon\gamma = 80.36$, provided that at 20° C. and measured wavelength $\infty$) is used as the coolant liquid in the cooling mechanism 120 in this embodiment. A plurality of coolant flowin-flowout portions 120A and 120B are arranged in symmetry on the peripheral end portion of the cooling emchanism 120, so that the flow direction of the coolant can be suitably selected. Designated at 111A and 112A are detachable flange portions.

In the fourth embodiment with the abovedescribed arrangement, a construction is provided which has satisfactory impedance matching, in which reflection is low from the exciting antenna 113 to the outer end of the electromagnetic lens section 116. Because of this, the electromagnetic waves delivered from means for generating the electromagnetic waves, such as a magnetron or the like, are efficiently focused and irradiated to the outside.

(Fifth Embodiment)

Figure 15:
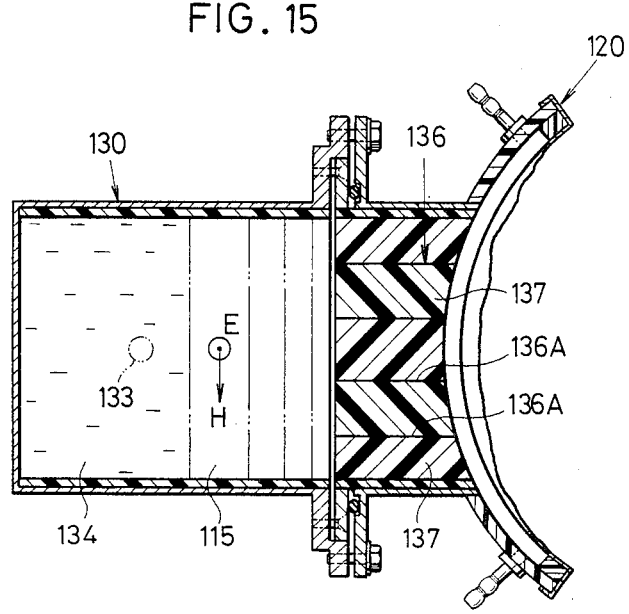
FIG. 15 is a sectional view showing a fifth embodiment of the present invention.

Description will hereunder be given of the fifth embodiment of the present invention with reference to FIG. 15.

This embodiment is one case where electromagnetic waves relatively low in frequency are used, wherein, particularly, the circumference of the exciting antenna 133 of the feed section is large and the feed section is filled up with a low loss dielectric material 134 such as oil. As shown in FIG. 15, the electromagnetic lens section 136 is used, the electromagnetic wave irradiation side of which is concavedly arranged. The spaces formed between the metal plates 136A, 136A, . . . constituting this electromagnetic lens section 136 are filled up with the low loss dielectric materials 137 different in dielectric constant from one another.

In this case, the dielectric materials relatively high in dielectric constant are disposed at the central portion and the dielectric materials relatively low in dielectric constant are disposed on the sides of the inner walls, so that the focusing of the electromagnetic waves can be performed effectively, the satisfactory matching with the living body can be attained and the case body 130 can be generally made conpact in size. The respects in the arrangement and the functional effects other than the above are identical with the fourth embodiment.

(Sixth Embodiment)

Figure 16:
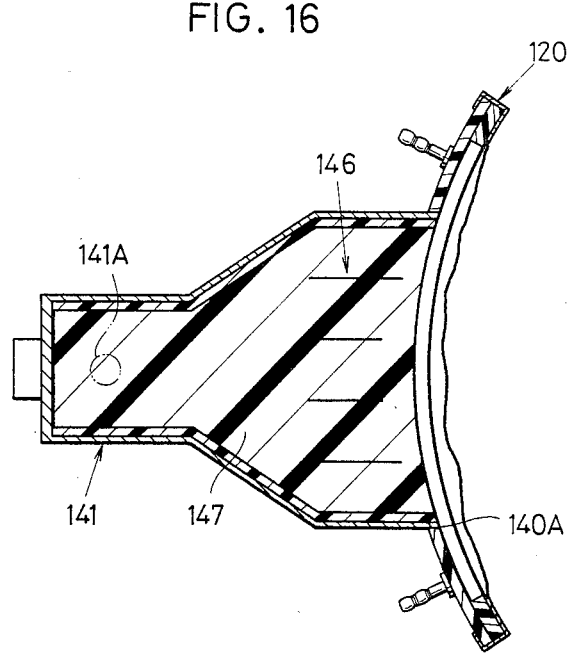
FIG. 16 is a sectional view showing a sixth embodiment of the present invention.

Description will hereunder be given of the sixth embodiment of the present invention with reference to FIG. 16.

In this embodiment shown in FIG. 16, designated at 140 is a case body and at 120 is a cooling mechanism similar to the one described above. The case body 140 is formed at one end thereof with a feed section 141. The electromagnetic waves which are output from this feed section 141 irradiate the living body from an irradiation opening 140A at the other end of the case body 140. In the case body 140, an electromagnetic lens section 146 is provided adjacent the irradiation opening 140A. A dielectric material 147 relatively high in dielectric constant and low in loss is uniformly filled up in the case body 140 over the entire area thereof. Denoted at 141A is an exciting antenna of the feed section. The respects in the specific arrangement of the cooling mechanism 120 are identical with those in the preceding embodiments.

The sixth embodiment is advantageous in that an applicator low in loss of the electromagnetic waves can be obtained through the action of the dielectric material 147, the embodiment can be generally made compact in size and the satisfactory matching with the living body can be attained.

In the fourth to sixth embodiments, the applicator used for heating wherein a cancer effected in the living body, is selected as an object has been described. However, in the case of selecting a cancer effected part on the surface of the living body as an object or heating an internal portion in the living body slowly, the cooling mechanism 120 is not needed.

(Seventh Embodiment)

Figure 17:
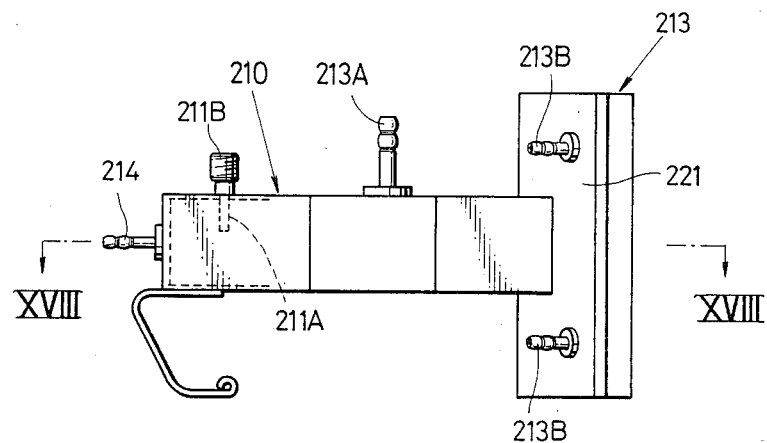
FIG. 17 is a front view showing a seventh embodiment of the present invention.
Figure 18:
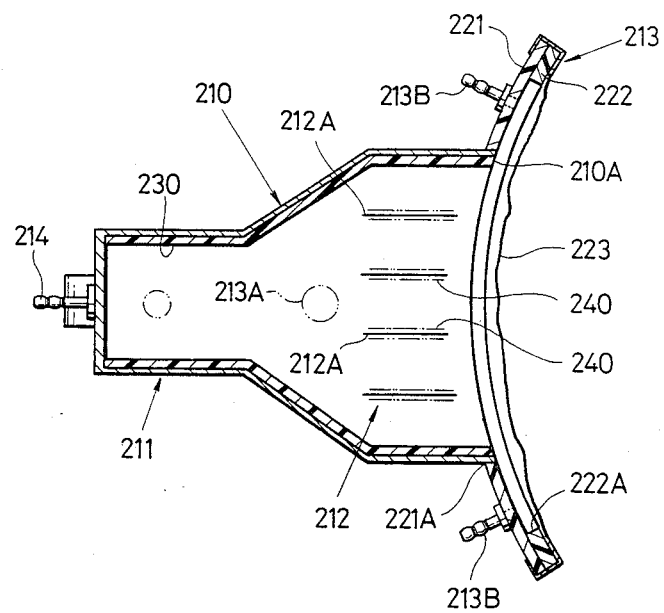
FIG. 18 is a sectional view taken along the line XVIII—XVIII in FIG. 17.
Figure 19:
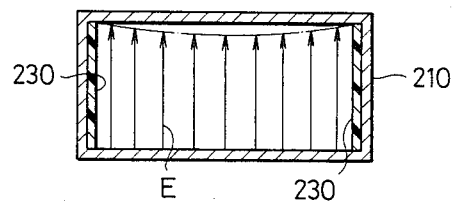
FIGS. 19(1), (2), (3) are explanatory views showing the uniformalizing of the field intensities through the action of the dielectric film, respectively.
Figure 19:
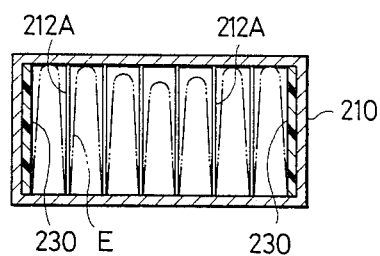
Figure 19:
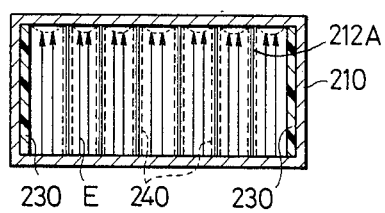

Description will hereunder be given of the seventh embodiment of the present invention with reference to FIGS. 17 to 19.

Referring to these drawings, designated at 210 is a case body functioning as a waveguide. A feed section 211 is provided at the left end portion of this case body 210 in the drawings, and an electromagnetic lens section 212 at the right end portion. Denoted at 211A is an exciting antenna, 211B a coaxial cable and 212A, 212A, . . . metal plates for the lens. A cooling mechanism 213 for the living body is provided at an electromagnetic wave irradiation opening 210A of this case body 210. The cooling mechanism 213 includes an abutment support plate 221 consisting of a dielectric plate curved along the living body (refer to A in FIG. 1), an abutting plate 222 solidly secured to the outer surface of the abutment support plate 221 and a flexible film member 223 sealedly mounted to the outer surface of the abutting plate 222. In the central portion of the abutment support plate 221, a square through-hole 221A abutting the irradiation opening 210A of the case body 210 is formed in the central portion of the abutment support plate 221, and a square cutaway hole 222A larger than this through-hole 221A is formed in the abutting plate 222 as shown in FIG. 18, so that the coolant liquid can very naturally flow between the interiors of the case body 210 and the cooling mechanism 213.

Water (relative dielectric constant $\epsilon \gamma = 80.36$, provided that at 20° C. and measured wavelength $\infty$) is used as the coolant liquid in the cooling mechanism 213 in this embodiment. A coolant flowin portion 213A for feeding the cooling water under pressure to the cooling mechanism 213 is provided at the center of the top surface of the case body 210 in FIG. 17, and coolant flowout portions 213B are provided at four corners of the abutment support plate 221 as shown in FIGS. 17 and 18, so that the coolant liquid can uniformly and effectivley cool the whole area from the interior of the case body 210 to the surface of the living body A.

As described above, the electromagnetic lens section 212 is formed of a plurality of metal plates 212A, 212A, . . . which are disposed equidistantly in such a manner that the metal plates disposed on the sides of the inner wall are longer than those disposed in the central portion, so that the effects of the lens can be fully utilized. The flexible film member 223 is provided on the outer end face of the cooling mechanism 213 for facilitating adhesion to the living body.

A dielectric plate 230 low in loss and relatively high in relative dielectric constant is provided on the inner wall of the case body 210 as shown in FIG. 18. In this case, the dielectric plate 230 is provided on the inner wall in parallel to the direction of the electric field of the electromagnetic waves. As the result, the field distribution in the case body is like one as shown in FIG. 19(1), whereby the energy of the electromagnetic waves is not concentrated at the center and is distributed substantially uniformly, so that the focusing function of the electromagnetic lens can be fully performed.

Figure 5:
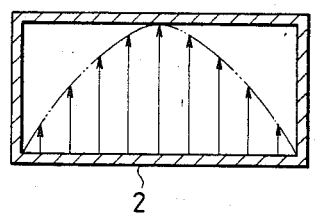
Figure 5:
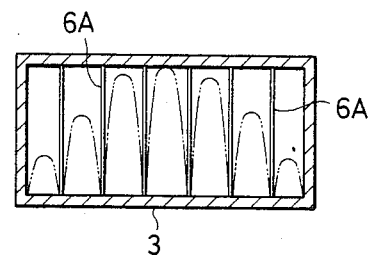

Each of the metal plates 212A, 212A, . . . of the electromagnetic lens 212 is provided thereon with a dielectric member 240 consisting of a member identical with the dielectric member 230 provided on the inner wall of the case body 210. Because of this, the concentration of the field distribution, which has been occurring in the electromagnetic lens section 212 as shown in FIGS. 5(2) and 19(2) is avoided and it becomes possible to set a field distribution as shown in FIG. 19(3). As the result, an ideal applicator for heating treatment can be obtained such that a grating-shaped overheat injury on the surface of the living body in the heating treatment corresponding to the field intensity can be prevented. It thus becomes possible to heat the surface (plane of incidence) of the living body uniformly and at a low temperature, and at the same time, a predetermiend portion in the living body can be concentratedly heated through the action of the electromagnetic lens.

Figure 20:
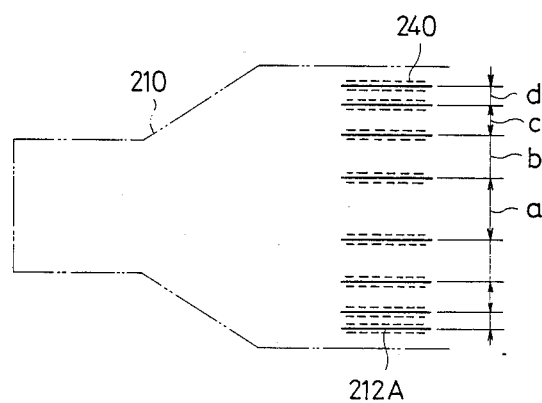
FIGS. 20 and 21 are views showing other electromagnetic lens sections, respectively.

Designated at 214 is liquid removing means for the deaerating. Besides the electromagnetic lens section 212 as shown in FIGS. 17 and 18, there may be used the electromagnetic lenses including one shown in FIG. 20, wherein the metal plates identical in dimensions with one another are used, however, the intervals between the metal plates are varied (provided that $$a > b > c > d \frac{\lambda}{2};$$

Figure 21:
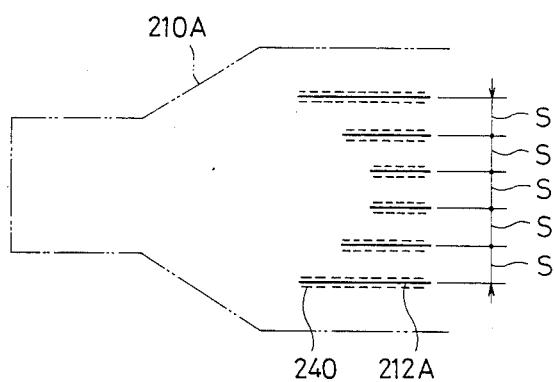

$\lambda$ is a wavelength), another one shown in FIG. 21, wherein the metal plates 212A on the sides of the inner wall are longer than ones in the central portion, and further, other various electromagnetic lenses.

(Eighth Embodiment)

Figure 22:
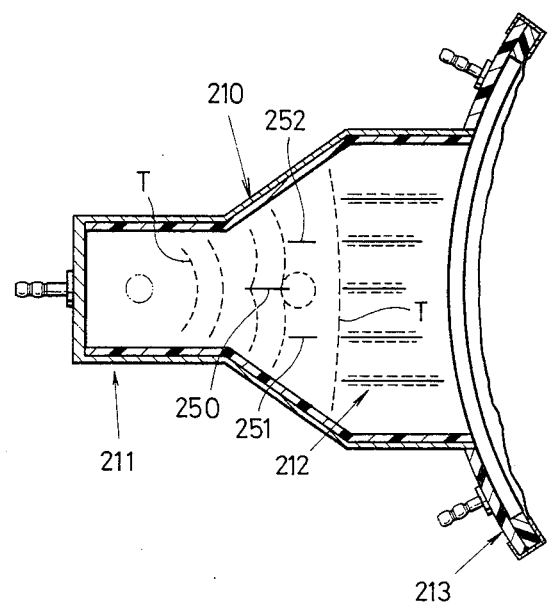
FIG. 22 is a sectional view showing an eighth embodiment of the present invention.

Description will hereunder be given of the eighth embodiment of the present invention with reference to FIG. 22.

In this embodiment, distributing plates 250, 251 and 252 for effectively dividing the electromagnetic waves are provided in the central portion of the case body 210, shown in the seventh embodiment, i.e. in a space formed between the feed section 211 and the electromagnetic lens section 212. The distributing plate 250 at the center of the distributing plates 250, 251 and 252 is projected toward the feed section 211 and the other distributing plates 251 and 252 are projected toward the electromagnetic lens section 212. The respects in the arrangement other than the above are identical with those in the prior art.

A broken line T in FIG. 22 indicates that the energy of the electromagnetic waves is effectively divided by the distributing plates 250, 251 and 252, so that the irradiation of the surface of the living body by the electromagnetic waves can be further uniform.

When the applicators shown in the seventh and eighth embodiments are used in slowly heating a part on the surface of the living body or a predetermined portion within the living body in particular, the cooling mechansim 213 may be removed.

(Ninth Embodiment)

Figure 23:
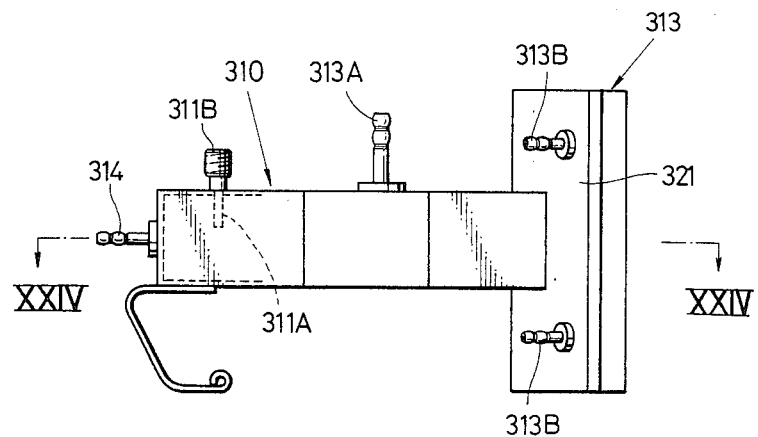
FIG. 23 is a front view showing a ninth embodiment of the present invention.
Figure 24:
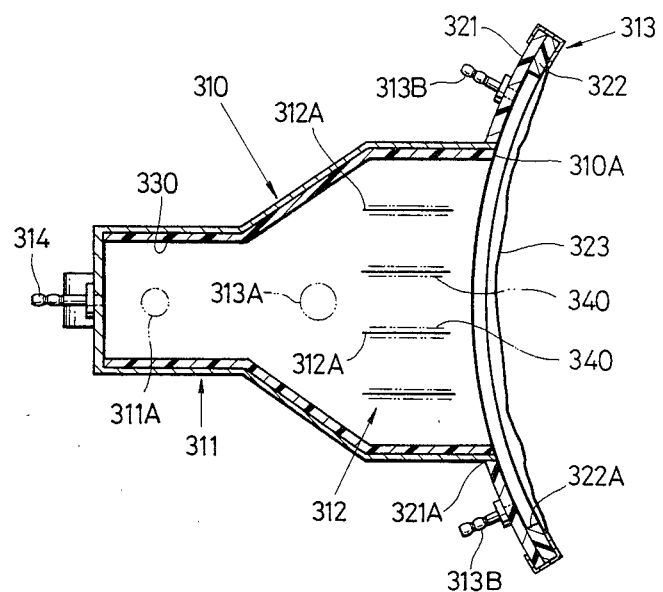
FIG. 24 is a sectional view taken along the line XXIV—XXIV in FIG. 23.

Description will hereunder be given of the ninth embodiment of the present invention with reference to FIGS. 23 and 24. Referring to these drawings, designated at 310 is a case body. The case body 310 functions as a waveguide, is provided at the left end portion thereof with an electromagnetic wave feed section 311 and at the right end portion thereof with an electromagnetic lens section 312. Denoted at 311A is an exciting antenna, 311B a coaxial cable, and 312A, metal plates constituting the electromagnetic lens section 312. Furthermore, a cooling mechanism 313 for cooling the living body is provided at an electromagnetic wave irradiation opening 310A of this case body 310. This cooling mechanism 313 includes an abutment support plate 321 formed of a dielectric plate curved along the living body (refer to A in FIG. 1), an abutting plate 322 solidly secured to the outer surface of this abutment support plate 321 and a flexible film member 323 sealedly mounted to the outer surface of the abutting plate 322. A square through-hole 321A abutting the irradiation opening 310A of the case body 310 is formed in the central portion of the abutment support plate 321 and, a square cutaway hole 322A larger than the through-hole 321A is formed in the abutting plate 322 as shown in FIG. 24, so that coolant liquid can very naturally flow between the interiors of the case body 310 and the cooling mechanism 313.

Water (relative dielectric constant $\epsilon\gamma = 80.36$, provided that at 20° C. and measured wavelength $\infty$) is used as the coolant liquid in the cooling mechanism 313. A coolant flowin-flowout portion 313A on one side for feeding the cooling water under pressure to the cooling mechanism 313 as necessary is provided at the center of the top surface of the case body 310 as shown in FIG. 23. Coolant flowin-flowout portions 313B at the other side are provided at four corners of the abutment support plate 321 as shown in FIGS. 23 and 24, so that the coolant liquid can uniformly and effectively cool the whole area from the interior of the case body 310 to the surface of the living body A.

The electromagnetic lens section 312 is constituted by a plurality of metal plates 312A, which are arranged equidistantly in such a manner that the metal plates disposed on the sides of the inner walls are longer than those disposed in the central portion, so that the effect of lens can be fully utilized. The flexible film member 323 is provided on the outer end face of the cooling mechanism 313 for facilitating the adhesion to the living body as described above.

On the other hand, a dielectric plate 330 low in loss and relatively high in relative dielectric constant is provided on the inner wall of the case body 310 as shown in FIG. 24. In this case, the dielectric plate 330 is provided on the inner wall in parallel to the direction of the electric field of the electromagnetic waves. As a result, the field distribution in the case body is like the one shown in FIG. 25(1), whereby the energy of the electromagnetic waves is not concentrated at the center and distributed substantially uniformly, so that the focusing function of the electromagnetic lens can be fully performed.

Figure 25:
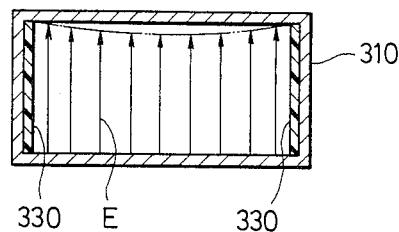
FIGS. 25(1), (2), (3) are explanatory views showing the uniformalizing of the field intensities through the action of the dielectric film, respectively.
Figure 25:
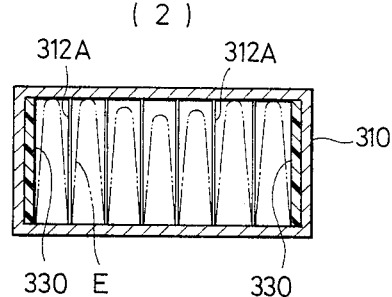
Figure 25:
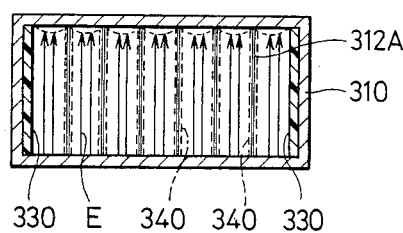

Each of the metal plates 312A, of the electromagnetic lens 312 is provided thereon with a dielectric member 340 identical in material with the dielectric member 330 provided on the inner wall of the case body 310. Because of this, the concentration of the field distribution occurring in the electromagnetic lens section 312 as shown in FIGS. 5(2) and 25(2) is avoided and it becomes possible to set a field distribution as shown in FIG. 25(3). As the result, an ideal applicator for the heating treatment can be obtained such that a grating-shaped overheat injury on the surface of the living body in the heating treatment corresponding to the field intensity can be prevented. It thus becomes possible to heat the surface (plane of incidence) of the living body uniformly and at low temperature and, at the same time, a predetermined portion within the living body can be concentratedly heated through the action of the electromagnetic lens.

Designated at 314 is liquid removing means for the deaerating the coolant liquid. This liquid removing means has a function of causing part of the coolant liquid to constantly flow to the outside, so that bubbles in the interior can be continuously released to the outside. Because of this, the disadvantage of the prior art of decreasing in output with time due to the influence of the bubbles can be improved to a considerable extent.

(Tenth Embodiment)

Figure 26:
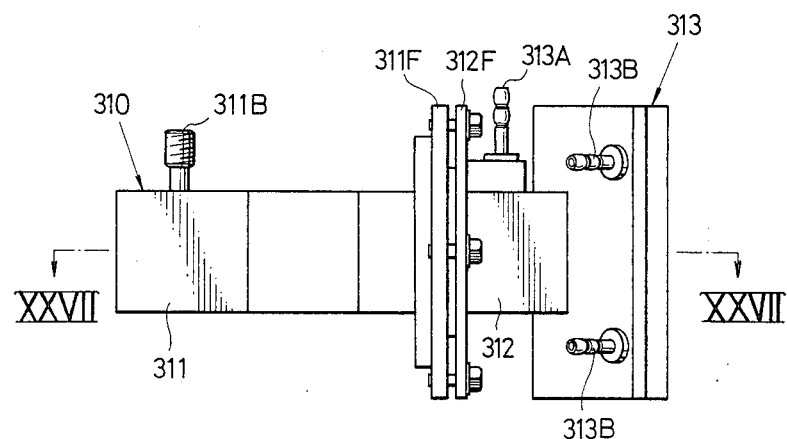
FIG. 26 is a front view showing a tenth embodiment of the present invention.
Figure 27:
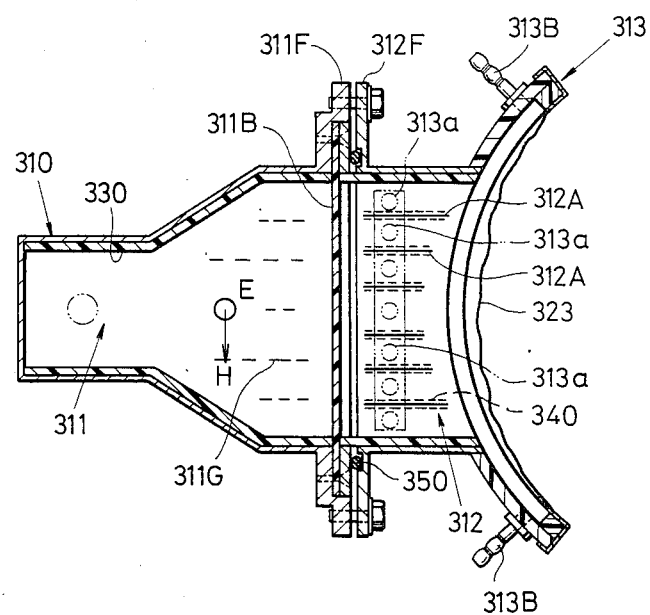
FIG. 27 is a sectional view taken along the line XXVII—XXVII in FIG. 26.

Description will hereunder be given of the tenth embodiment of the present invention with reference to FIGS. 26 and 27.

In this embodiment, the electromagnetic wave feed section 311 and the electromagnetic lens section 312, as in the first embodiment, are separated from each other and detachably connected to each other and the electromagnetic wave feed section 311 is filled up with a material 311G low in attenuation such as machine oil. Denoted at 311B is a sealing partition plate. The coolant flowin-flowout portion 313A on one side in the ninth embodiment (refer to FIGS. 23 and 24) is a plurality of branched flowin-flowout ports 313a in the case body 310 in this embodiment. More specifically, the respective flowin-flowout ports 313a are provided above the center portions between the metal plates 312A constituting the electromagnetic lens section 312, so that the cooling water can flow substantially uniformly into the electromagnetic lens section 312 of the case body 310 such that the electric field of the electromagnetic waves is not disturbed at all. Designated at 311F and 312F are flange portions for the connection and 350 is a seal member. Except that this embodiment has no liquid removing means for deaerating, the respects in the arrangement other than the above are identical with those in the first embodiment.

(Eleventh Embodiment)

Figure 28:
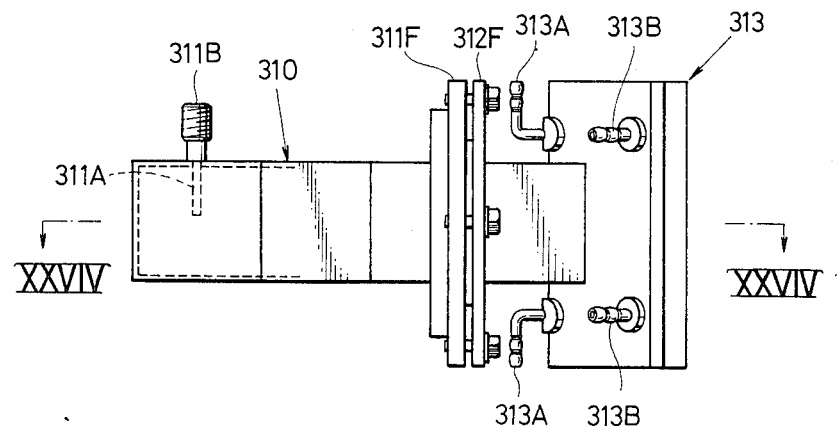
FIG. 28 is a front view showing an eleventh embodiment of the present invention.
Figure 29:
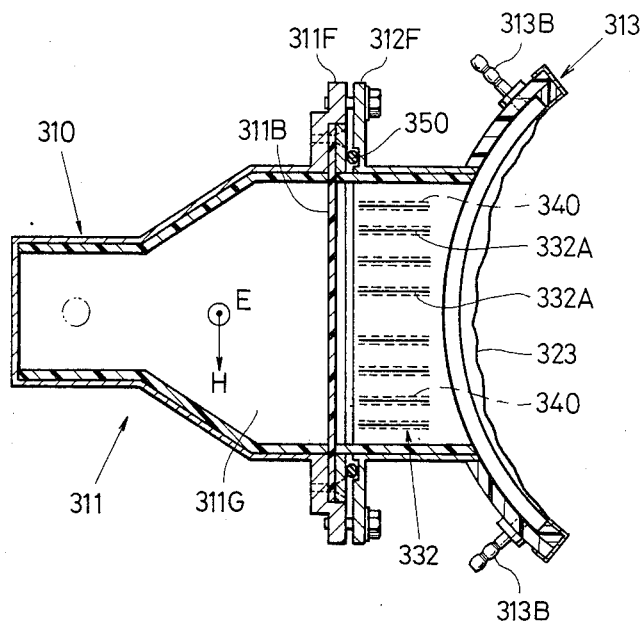
FIG. 29 is a sectional view taken along the line XXIX—XXIX in FIG. 28.

Description will hereunder be given of the eleventh embodiment of the present invention with reference to FIGS. 28 and 29.

This embodiment is identical with the tenth embodiment except that the coolant flowin-flowout means 313A on one side in the tenth embodiment is provided at the top and bottom end portions at the center of the rear surface of the cooling mechanism 313 without being branched in this embodiment, as shown in FIG. 28 and the metal plates 332A having the dimensions identical with one another are used in the electromagnetic lens section 332. In this case, the intervals between the metal plates 332A are decreased toward the peripheral portion in the electromagnetic lens portion 332, whereby the passing electromagnetic waves are varied in phase velocity, so that the effect of lens can be fully performed. The cooling water also flows from the substantially central portion of the cooling mechanism 313 toward the peripheral portion of the cooling mechanism 313, so that the cooling water can effectively cool the surface of the living body in the same manner as in the preceding embodiments.

In the ninth to eleventh embodiments, examples have been given of the cases where the flow course of the coolant liquid is directed from the central portion of the cooling mechanism 313 toward the peripheral poriton. However, the present invention need not necessarily be limited to this, and such an arrangement may be adopted where the coolant liquid is caused to flow in a direction opposite to the one shown in the preceding embodiments.

(Twelfth Embodiment)

Description will hereunder be given of the twelfth embodiment of the present invention with reference to FIGS. 30 to 35.

Figure 1:
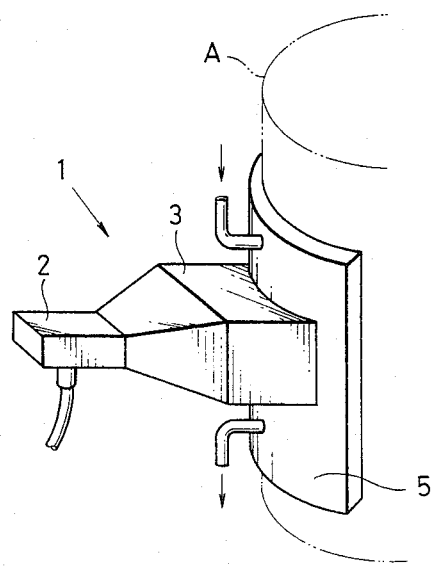

Referring to these drawings, designated at 410 is a case body functioning as a waveguide, and at 411 is a cooling mechanism for cooling the surface of the living body A (refer to A in FIG. 1). The case body 410 is provided at the left end portion thereof with an electromagnetic wave feed section 412 and in a segmental portion at the right end portion thereof with an electromagnetic lens section 413, in FIG. 30. The case body 410 is filled up with a liquefied dielectric material additionally functioning as a coolant, and an arrangement is adopted such that, as will be described hereunder, the liquefied dielectric material can flow from the side of the case body 410 to an irradiation opening 410A on the side of the electromagnetic wave irradiation.

Figure 31:
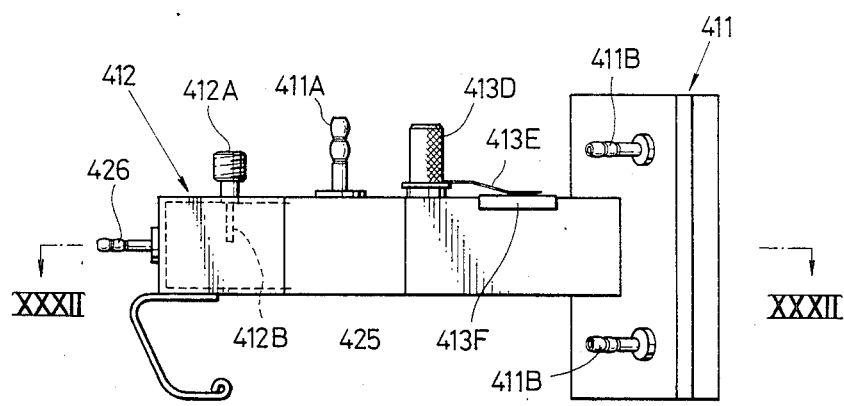
FIG. 31 is a front view of FIG. 30.
Figure 32:
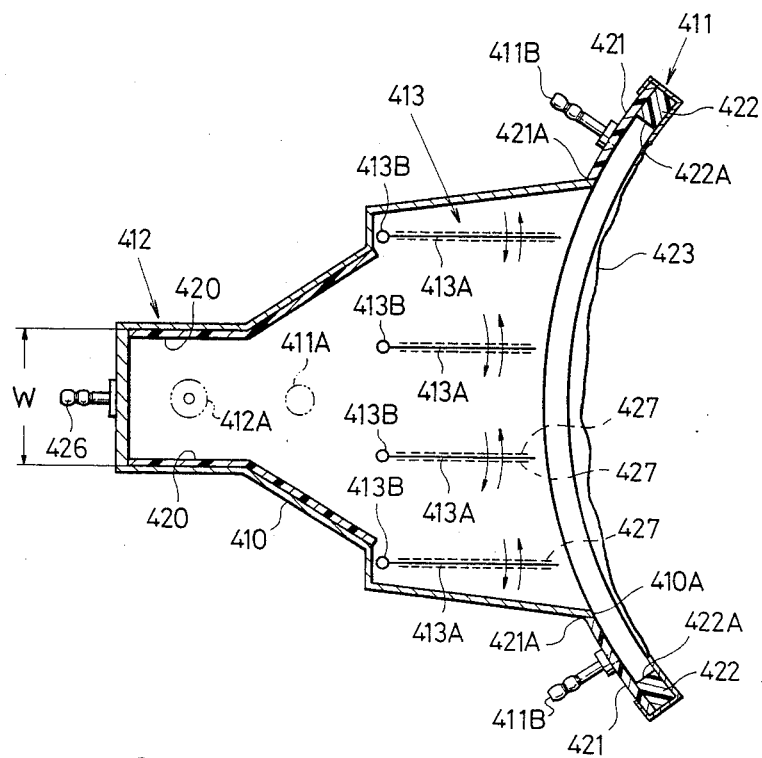
FIG. 32 is a sectional view taken along the XXXII—XXXII in FIG. 31.
Figure 33:
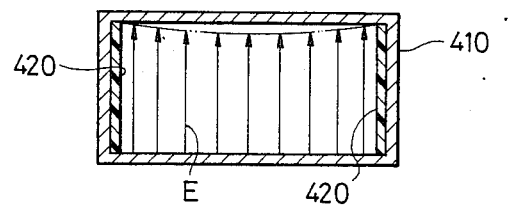
FIG. 33 is an explanatory view showing the field distribution in the feed section in looking from the right in FIG. 32.

As shown in FIG. 32, the size of the feed section 412 is determined such that the width W of the feed section 412 is set to the size of ½-1 wavelength of the electromagnetic waves in the coolant liquid. Designated at 412A is a coaxial connector and at 412B is (refer to FIG. 31) an exciting antenna. A dielectric plate 420 low in loss and relatively high in relative dielectric constant is provided on a portion of the inner wall surface of this feed section 412 as shown in FIG. 32, the portion being in parallel to the direction E of the electric field of the electromagnetic waves, so that the field distribution can be made uniform as will be described hereunder. This dielectric plate 420 is extended to the inner wall of the case body 410.

The cooling mechanism 411 includes an abutment support plate 421 consisting of a dielectric plate curved along the living body (refer to A in FIG. 1), an abutting plate 422 solidly secured to the outer surface of this abutment support plate 421 and a flexible film member 423 sealedly mounted to the outer surface of the abutting plate 422. In the central portion of the abutment support plate 421, a square through-hole 421A abutting an irradiation opening 410A of the case body 410 is formed in the central portion of the abutment support plate 421, and a square cutaway hole 422A larger than this through-hole 421A is formed in the abutting plate 422 as shown in FIG. 32, so that the coolant liquid can very naturally flow between the interiors of the case body 410 and the cooling mechanism 411.

Figure 30:
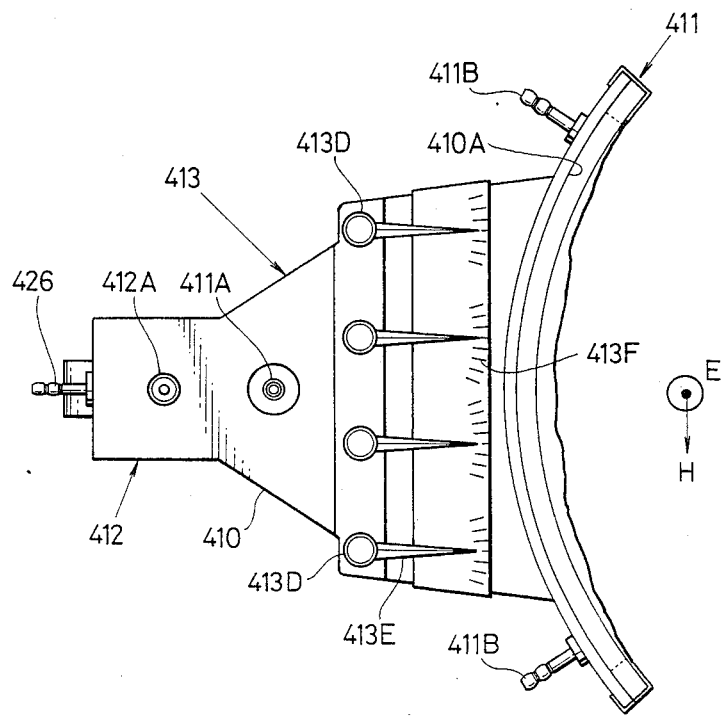
FIG. 30 is a plan view showing a twelfth embodiment of the present invention.

Water (relative dielectric constant $\epsilon\gamma = 80.36$, provided that at 20° C. and measured wavelength $\infty$) is used as the coolant liquid in the cooling mechanism 411 in this embodiment. A coolant flowin portion 411A for feeding the cooling water to the cooling mechanism 411 is provided at the center of the top surface of the case body 410 in FIG. 30, and coolant flowout portions 411B are provided at four corners of the abutment support plate 421, as shown in FIGS. 30 to 32, so that the coolant liquid can uniformly and effectively cool the whole area from the interior of the case body 410 to the surface of the living body A.

Figure 2:
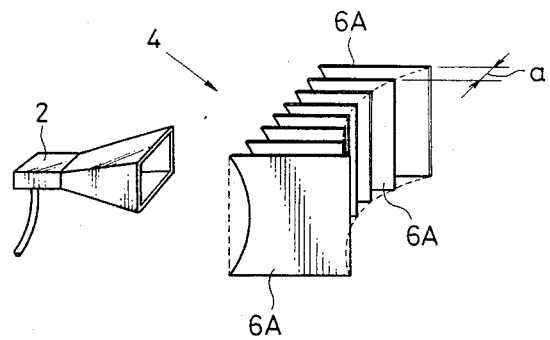
Figure 3:
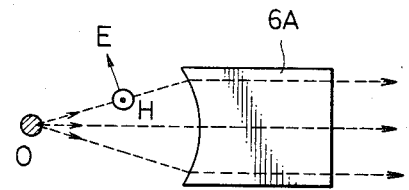
Figure 4:
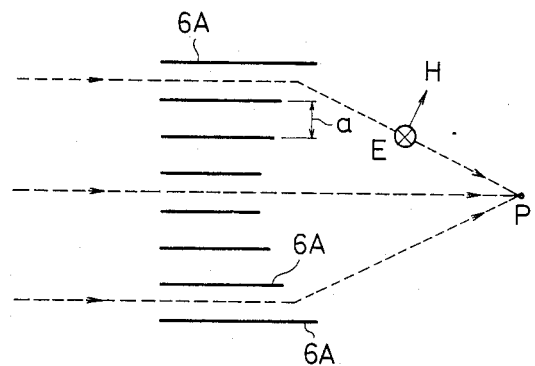

The electromagnetic lens section 413 is constituted by a plurality of metal plates 413A. Rotational pivot points 413B, are solidly secured to the ends of the metal plates 413A on the sides of the feed sections, respectively, and these rotational pivot points 413B are rotatably mounted to the case body 410. A rotation locking means 425 of a fitting type construction are provided on the rotational pivot points 413B on the side of the case body 410 through spring seats, not shown, in this embodiment, so that each of the metal plates 413A can rotate freely within a predetermined scope and locked at a desired position. Designated at 413D is a turning grip used in this case, 413E a pointer and 413F an angle dial, respectively. To describe the electromagnetic lens section 413 further in detail, the metal plates of the electromagnetic lens section 413 used in this embodiment are identical with one shown in the examples of the prior art (refer to FIGS. 2 to 4). On the other hand, in the electromagnetic lens section 413, an arrangement may be adopted wherein the metal plates 413A having dimensions identical with one another and disposed at different intervals (provided that $$a > b > c > \frac{\lambda}{2};$$

Figure 34:
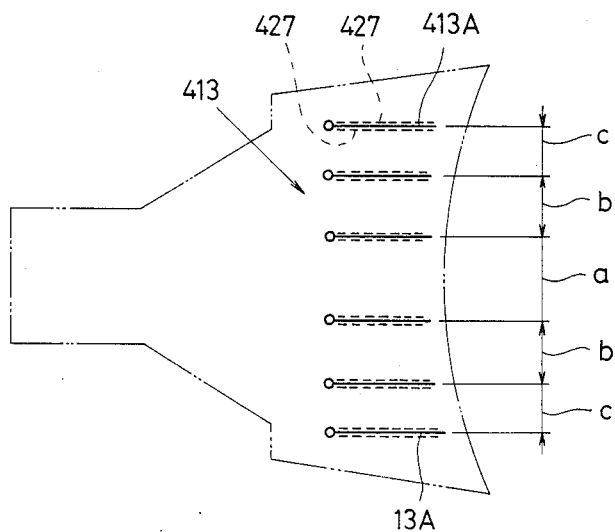
FIGS. 34 and 35 are general plan views showing other examples of the electromagnetic lens section, respectively.

$\lambda$ is a wavelength) as shown in FIG. 34. Further, another arrangement is possible wherein the metal plates are disposed at regular intervals S, the ends of the metal plates on the sides of the irradiation opening 410A are on one and the same line as indicated by a dotted line, and the shorter metal plates are disposed in the central portion and the longer metal plates are disposed on the sides of the inner wall (provided that $$S > \frac{\lambda}{2}$$

Figure 35:
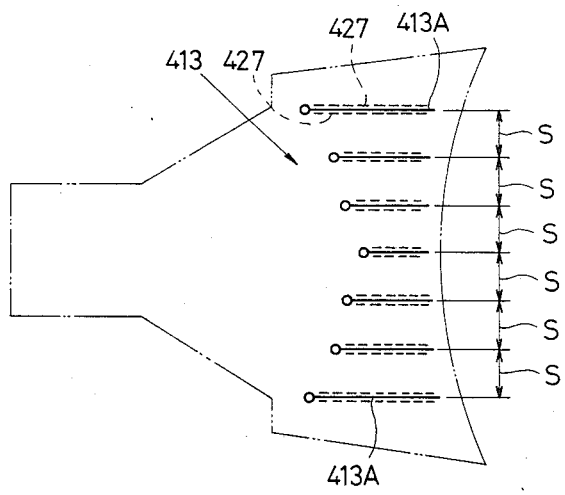

As shown in FIG. 35. In in the electromagnetic lens section 413 shown in FIG. 34, the narrower the interval between the metal plates 413A is, the faster the phase velocity of the electromagnetic wave is. While in the electromagnetic lens portion 413 shown in FIG. 35, the phase of the electromagnetic waves progresses in the plane of irradiation in an area where the metal plates 413A are longer. Consequently, in either case, the electrostatic lens functions effectively.

A liquid removing portion 426 for the deaerating is provided at the center of the outer end portion of the feed section 412 (at the left end portion in FIG. 30). When necessary, this removing portion 426 allows a predetermined amount of the coolant liquid to intermittently flow out or permits a very small amount of the coolant liquid to continuously flow out, so that bubbles being produced in the interior at the same time as above can be discharged to the outside.

Denoted at 427, 427, . . . are dielectric films pasted on the metal plates 413A of the electromagnetic lens section 413. This dielectric film 427 is formed of a dielectric member having the characteristics identical with the one pasted on the inner wall of the case body 410. Because of this, in this electromagnetic lens section 413, an electric field effect similar to the one shown in FIG. 33 can be obtained, whereby temperature on the heated surface of the living body A is made more uniform, so that a pain of a patient due to partial overheat during the heating treatment can be further relieved.

In this embodiment, water (relative dialectric constant $\epsilon\gamma = 80.36$, provided that at 20° C., measured wavelength $\infty$) is used as the coolant liquid. In consequence, such advantages can be offered in that the dimensions of the case body 410 and electromagnetic lens 413 are made as small as about $1\sqrt{80.36}$ times the dimensions of the case body and electromagnetic lens, both of which would enclose therein air, and the matching with the living body is improved.

Description will hereunder be given of general action of the embodiment. First of all, the electromagnetic waves delivered into the case body 410 from the exciting antenna 412B are made uniform in field intensity through the action of the dielectric plate 420 provided on the inner wall of the feed section 412. Thus the energy of the electromagnetic waves does not concentrate at the central portion, and is substantially uniform in the cross section of the case body 410, and delivered to the electromagnetic lens section 413. Because of this, in the electromagnetic lens section 413, the lens effect on the electromagnetic waves is effectively displayed to deliver the focusing electromagnetic waves toward the irradiation opening 410A. This irradiation opening 410A is disposed close to the living body A through the coolant liquid of the cooling mechanism 411 and dielectric film 423, so that the focal point of the electromagnetic lens 413 can be formed in a deep portion of the living body A. Because of this, it becomes possible to effectively heat the deep portion rather than the surface of the living body. The surface of the living body absorbs the electromagnetic waves to a considerable extent, whereby elevation of temperature is relatively high, setting aside the lens effect described above. As against this, not only the surface of the living body, but also elevated temperature in the case body 410 due to Joule loss and dielectric loss can be effectively cooled by the flowin and flowout of the coolant liquid through the cooling mechanism 411. In this case, the dielectric films 420 and 427 provided on the inner wall of the case body 410 and the metal plates 413A of the electromagnetic lens 413 form a substantially uniform electric field in a cross section perpendicularly intersecting the proceeding direction of the electromagnetic waves, so that the energy of the electromagnetic waves can be also substantially uniform. Because of this, uniformity can be attained in the temperature of heating the surface of the living body, so that the disadvantage in the example of the prior art that overheating progresses in the central portion of the surface of the living body rather than the portion around the central portion can be improved to a considerable extent.

Figure 38:
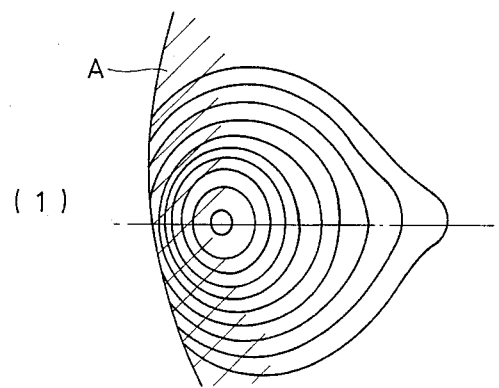
FIGS. 38(1), (2) are explanatory views showing the results of experiments of the twelfth embodiment of the present invention, respectively.
Figure 38:
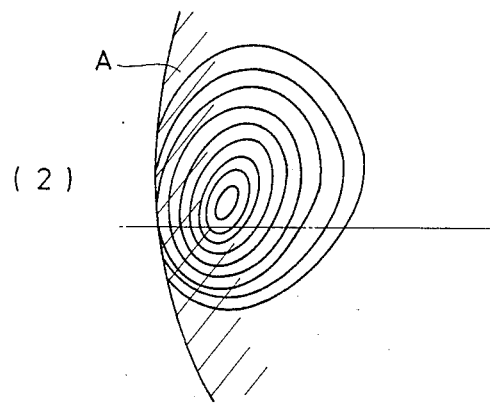

Description will now be given of action when the electromagnetic lens section 413 is rotated with reference to FIG. 38. FIGS. 38(1) and 38(2) show the results of experiments of heating, in which phantom models each having an electric and a thermal constants equivalent in value to those of the living body, are used. FIG. 38(1) shows a heating pattern when the metal plates 413A, are set in parallel to the center axis of the case body 410 (with no inclinations), while FIG. 38(2) shows a heating pattern when the irradiation opening 410A on one side is closed, as for an extreme case (provided that an isothermal line $\Delta T = 1°$ C., radius of each of the models is 125 mm and temperature of liquid is constantly at 20° C.).

As the result, it has become apparent that variable irradiation by the electromagnetic lens 413 is adopted, whereby the central portion of the heated deep portion is easily moved, so that the electromagnetic waves of a cancerous tissue in a relatively large scope can be caught substantially uniformly and the electromagnetic waves of a cancerous tissue in a position present at one side can be reliably caught by the central portion of the focus.

(Thirteenth Embodiment)

Figure 36:
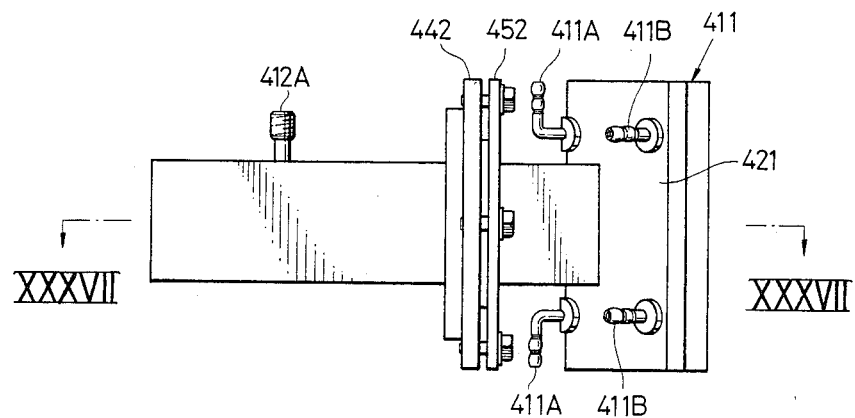
FIG. 36 is a front view showing a thirteenth embodiment of the present invention.
Figure 37:
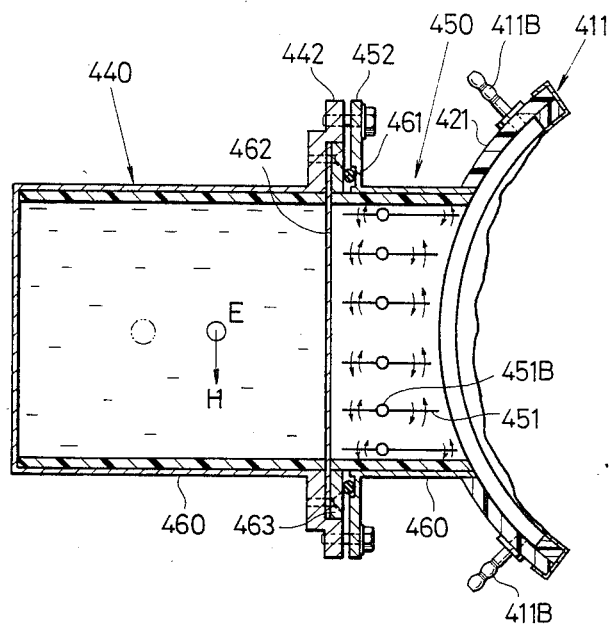
FIG. 37 is a sectional view taken along the line XXXVII—XXXVII in FIG. 36.

Description will hereunder be given of the thirteenth embodiment of the present invention with reference to FIGS. 36 and 37.

This thirteenth embodiment is constructed such that the feed section 440 and the electromagnetic lens section 450 are detachable from each other, whereby it is contemplated that a plurality of electromagnetic lens sections 450 are prepared in advance and the optimum electromagnetic lens section 450 can be selectively used at all times.

In this embodiment, the feed section 440 is filled up with oil having a relative dielectric constant $\epsilon\gamma \approx 25$. This oil is selected such that it is very low in attenuation of the electromagnetic waves. On the other hand, fulcrums of rotation 451B, of the metal plates 451 in the electromagnetic lens section 450 are provided at the substantially central portions of the metal plates 451, so that the metal plates 451 can be rotated smoothly. In this embodiment, the coolant flowin portions 411A are provided at the centers (on the center axis of the case body 460) of the top and bottom end portions of the abutment support plate 421 in FIG. 36, whereby the coolant liquid flows through the end of the central portion and the surface of the living body A, and into the electromagnetic lens section 450, flows out from the four corners of the cooling mechanism 411 in the same manner as described above. If the flowin and flowout directions of the coolant liquid are suitably changed as necessary, then the deaerating can be effectively performed. Designated at 442 and 452 are connecting flange portions for detachment, 461 a seal member and 462 an oil sealing plate. Furthermore, this oil sealing plate 462 is fixed at the peripheral position thereof to the feed section 440 through a fixing frame 463. The respects in the arrangement other than the above are identical with those in the twelfth embodiment.

As described above, according to the thirteenth embodiment, substantially the same functional effects in the twelfth embodiment can be attained. Moreover, the energy of the electromagnetic waves can be efficiently delivered into the living body because the oil, which is very low in dielectric loss, is sealed in the feed section 440 in particular, so that any one of the prepared electromagnetic lens sections matching the shape of the living body can be selectively used.

In this thirteenth embodiment, the dielectric material use to fill up the feed section 440 need not necessarily be limited to oil, and any other liquefied or solid dielectric material will do, only if the material is low in attenuation of the electromagnetic waves and high in dielectric constant.

In the above-described twelfth and thirteenth embodiments, the cooling mechanism 411 may be a flat one. The coolant flowin portions 411A may be provided at the central portions between the respective metal plates of the electromagnetic lens sections 413 and 450. A method may be adopted such that all of the metal plates 413A or 451 of the electromagnetic lens section 413 or 450 may be driven at the same time by the driving of a motor or the like. In this case, the rotation locking means may be additionally functioned by a drive transmission means.

Furthermore, in treating a cancer of the skin, the cooling mechanism 411 can be dispensed with.

As has been described hereinabove, the embodiments of various types of the present invention have been disclosed, and any one of which displays the significant role in the treatment of heating a portion of a cancer in the living body. It becomes possible to efficiently and rapidly perform the heating treatment by the suitable selective use of any one of the embodiments matching the position, size and the like of the living body.

What is claimed is:

1. An applicator for applying a heating treatment to a body comprising:
   a. a waveguide case for guiding electromagnetic waves towards said body;
   b. an electromagnetic wave feed section formed at one end of said waveguide case for feeding said electromagnetic waves towards said body;
   c. an opening formed at a second end of said waveguide case for delivering said electromagnetic waves to said body;
   d. an electromagnetic lens section positioned in said waveguide case between said electromagnetic feed section and said opening for focusing said electromagnetic waves towards said body; and
   e. a coolant liquid circulation system connected to said electromagnetic lens section for circulating coolant liquid into and out of said electromagnetic lens section.

2. The applicator as set forth in claim 1 wherein said electromagnetic lens section comprises a plurality of metal plates for focusing said electromagnetic waves.

3. The applicator as set forth in claim 2 wherein said plurality of metal plates are positioned at substantially equal distances from one another.

4. The applicator as set forth in claim 3 wherein one of said plurality of metal plates positioned nearer to inner walls of said waveguide case are longer than other ones of said plurality of metal plates positioned in a central portion of said waveguide case.

5. The applicator defined by claim 2 further comprising electromagnetic wave distributing plates for substantially uniformly distributing the electromagnetic waves delivered to said electromagnetic lens section wherein said plates are interposed between said electromagnetic wave feed section and said electromagnetic lens section.

6. An applicator for a heating treatment as set forth in claim 1, wherein a plurality of metal plates constituting said electromagnetic lens section are formed to have dimensions equal to one another and intervals between said metal plates disposed close to the inner walls of said case are made narrower than those disposed in the central portion of said case.

7. The applicator defined by claim 1 wherein said electromagnetic lens section comprises a plurality of metal plates arranged at predetermined regular intervals and wherein said applicator further comprises a plurality of dielectric plates provided on opposite surfaces of each of said metal plates.

8. The applicator defined by claim 1 further comprising a plurality of metal plates comprising said electromagnetic lens section which are mounted on said waveguide case in a manner so as to be rotatable within a predetermined scope.

9. The applicator defined by claim 1 further comprising: a cooling mechanism for cooling the surface of a living body provided at the opening of said case; wherein said coolant circulation system causes the coolant liquid to flow into and out of an inner portion of said case wherein said system is connected to said case through said cooling mechanism, said case having said electromagnetic lens section and said electromagnetic wave feed section; wherein said coolant liquid flows through the entire area of the interior of said case including said electromagnetic wave feed section.

10. An applicator for applying a heating treatment to a body comprising:
    a. a waveguide case for guiding electromagnetic waves towards said body;
    b. an electromagnetic wave feed section formed at one end of said waveguide case for feeding said electromagnetic waves towards said body;
    c. an opening formed at a second end of said waveguide case for delivering said electromagnetic waves to said body;
    d. an electromagnetic lens section positioned in said waveguide case between said electromagnetic feed section and said opening for focusing said electromagnetic waves towards said body;
    e. a coolant liquid circulation system connected to said electromagnetic lens section for circulating coolant liquid into and out of said electromagnetic lens section, and
   wherein said electromagnetic wave feed section includes a dielectric material which is relatively low in attenuation of electromagnetic waves and has a relatively high dielectric constant.

11. The applicator as set forth in claim 10 wherein said dielectric material comprises a fluid material and further comprising a dielectric sheet is provided at an open end of said electromagnetic wave feed section for sealing said fluid material in said electromagnetic wave feed section.

12. An applicator for applying a heating treatment to a body comprising:
   a. a waveguide case for guiding electromagnetic waves towards said body;
   b. an electromagnetic wave feed section formed at one end of said waveguide case for feeding said electromagnetic waves towards said body;
   c. an opening formed at a second end of said waveguide case for delivering said electromagnetic waves to said body;
   d. an electromagnetic lens section positioned in said waveguide case between said electromagnetic feed section and said opening for focusing said electromagnetic wave towards said body;
   e. a coolant liquid circulation system connected to said electromagnetic lens section for circulating coolant liquid into and out of said electromagnetic lens section, and
   f. deaerating means provided on a portion of said waveguide case and communicating with said electromagnetic lens section for removing bubbles from said coolant liquid.

13. An applicator for applying a heating treatment to a body comprising:
   a. a waveguide case for guiding electromagnetic waves towards said body;
   b. an electromagnetic wave feed section formed at one end of said waveguide case for feeding said electromagnetic waves towards said body;
   c. an opening formed at a second end of said waveguide case for delivering said electromagnetic waves to said body;
   d. an electromagnetic lens section positioned in said waveguide case between said electromagnetic feed section and said opening for focusing said electromagnetic waves towards said body;
   e. a coolant liquid circulation system connected to said electromagnetic lens section for circulating coolant liquid into and out of said electromagnetic lens section, and
   wherein said electromagnetic wave feed section and said electromagnetic lens section form two divided sections, said two sections being detachably connected to one another.

14. An applicator for applying a heating treatment to a body comprising:
   a. a waveguide case for guiding electromagnetic waves towards said body;
   b. an electromagnetic wave feed section formed at one end of said waveguide case for feeding said electromagnetic waves towards said body;
   c. an opening formed at a second end of said waveguide case for delivering said electromagnetic waves to said body;
   d. an electromagnetic lens section positioned in said waveguide case between said electromagnetic feed section and said opening for focusing said electromagnetic waves towards said body;
   e. a cooling mechanism provided at said opening of said waveguide case for cooling a surface of said body; and
   f. a coolant circulation system connected to said electromagnetic lens sections through said cooling mechanism for circulating coolant liquid into and out of said electromagnetic lens section.

15. An applicator for applying a heating treatment to a body comprising:
   a. a waveguide case for guiding electromagnetic waves towards said body;
   b. an electromagnetic wave feed section formed at one end of said waveguide case for feeding said electromagnetic waves towards said body;
   c. an opening formed at a second end of said waveguide case for delivering said electromagnetic waves to said body;
   d. an electromagnetic lens section positioned in said waveguide case between said electromagnetic feed section and said opening for focusing said electromagnetic waves towards said body;
   e. a coolant circulation system connected to said electromagnetic lens sections for circulating coolant liquid into and out of said electromagnetic lens section; and
   f. a dielectric plate positioned along an inner wall of said electromagnetic wave feed section on a plane which is parallel to an electric field component of said electromagnetic waves output from said electromagnetic wave feed section.

16. An applicator for applying a heating treatment to a body comprising:
   a. a waveguide case for guiding electromagnetic waves towards said body;
   b. an electromagnetic wave feed section formed at one end of said waveguide case for feeding said electromagnetic waves towards said body;
   c. an opening formed at a second end of said waveguide case for delivering said electromagnetic waves to said body;
   d. an electromagnetic lens section positioned in said waveguide case between said electromagnetic feed section and said opening for focusing said electromagnetic waves towards said body;
   e. a cooling mechanism provided at said opening of said waveguide case for cooling a surface of said body; and
   f. a coolant circulation system connected to said electromagnetic lens sections through said cooling mechanism for circulating coolant liquid into and out of said electromagnetic lens section; and
   g. a flexible dielectric sheet sealingly mounted to said cooling mechanism on a side of said cooling mechanism which contacts said surface, said flexible dielectric sheet being relatively low in attenuation of said electromagnetic waves.

* * * * *